(12) United States Patent
Shimizu et al.

(10) Patent No.: US 10,005,712 B2
(45) Date of Patent: Jun. 26, 2018

(54) METHOD FOR CHEMICAL CONVERSION OF UNSATURATED FATTY ACID BY CARBON CHAIN EXTENSION REACTION

(71) Applicant: Bizen Chemical Co., Ltd., Okayama (JP)

(72) Inventors: Yoshio Shimizu, Okayama (JP); Naomichi Bamba, Okayama (JP); Mitsumasa Mankura, Okayama (JP)

(73) Assignee: BIZEN CHEMICAL CO., LTD., Okayama (JP)

( * ) Notice: Subject to any disclaimer, the term of this patent is extended or adjusted under 35 U.S.C. 154(b) by 0 days. days.

(21) Appl. No.: 15/116,176

(22) PCT Filed: Jan. 14, 2015

(86) PCT No.: PCT/JP2015/000130
§ 371 (c)(1),
(2) Date: Aug. 2, 2016

(87) PCT Pub. No.: WO2015/115032
PCT Pub. Date: Aug. 6, 2015

(65) Prior Publication Data
US 2017/0166512 A1    Jun. 15, 2017

(30) Foreign Application Priority Data

Feb. 3, 2014    (JP) .................. 2014-018354

(51) Int. Cl.
*C07C 51/00*    (2006.01)
*C07C 67/24*    (2006.01)
*C07C 51/353*    (2006.01)

(52) U.S. Cl.
CPC ............ *C07C 67/24* (2013.01); *C07C 51/353* (2013.01)

(58) Field of Classification Search
CPC ..................................................... C07C 67/24
(Continued)

(56) References Cited

FOREIGN PATENT DOCUMENTS

| JP | 56-16442 A | 2/1981 |
| JP | 8/245508 A | 9/1996 |
| JP | 8245508 A * | 9/1996 |

OTHER PUBLICATIONS

Brown, Richard T., "Dealkoxycarbonylation of representative Beta-keto-esters and Beta-diesters in alkanoic acids," Journal of Chemical Research, Synopses, 1984, pp. 332-333.*

(Continued)

*Primary Examiner* — Deborah D Carr
(74) *Attorney, Agent, or Firm* — Seed IP Law Group LLP

(57) ABSTRACT

The present invention relates to a method for the chemical conversion of an unsaturated fatty acid, particularly a carbon chain extension reaction. According to the present invention, a method for extending the length of a carbon chain in an unsaturated fatty acid by two carbon atoms is provided, said method comprising a step of heating a malonic acid ester derivative of an unsaturated fatty acid to reflux in a lower fatty acid solution in the presence of an antioxidative agent. It is preferred that the unsaturated fatty acid is an unsaturated fatty acid having 16 to 24 carbon atoms. It is preferred that the unsaturated fatty acid is selected from the group consisting of linoleic acid, linolenic acid, arachidonic acid, stearidonic acid, icosatetraenoic acid, icosapentaenoic acid, tetracosahexaenoic acid and docosahexaenoic acid. According to the method of the present invention, a carbon chain extension reaction can be completed within a shorter time.

7 Claims, 2 Drawing Sheets

(58) Field of Classification Search
USPC ......................................................... 554/163
See application file for complete search history.

(56) References Cited

OTHER PUBLICATIONS

Brown et al., "Dealkoxycarbonylation of Representative β-Keto-esters and β-Diesters in Alkanoic Acids," *J. Chem. Research (Synopsis)*:332-333, 1984.

Haider et al., "Synthesis of Phosphatidylcholine Having a Very Long Chain Polyunsaturated Fatty Acid," *Chemistry Letters* 27(2):175-176, 1998.

International Preliminary Report on Patentability (translation), dated Aug. 4, 2016, for International Application No. PCT/JP2015/000130, 7 pages.

Baba et al., "A first synthesis of a phosphatidylcholine bearing docosahexaenoic and tetracosahexaenoic acids," *J. Chem. Soc., Perkin Trans.* 1:221-223, 2001.

Brown et al., "Dealkoxycarbonylation of Representative β-Keto-esters and β-Diesters in Alkanoic Acids," *J. Chem. Research* (S):332-333, 1984.

* cited by examiner

[Fig. 1]
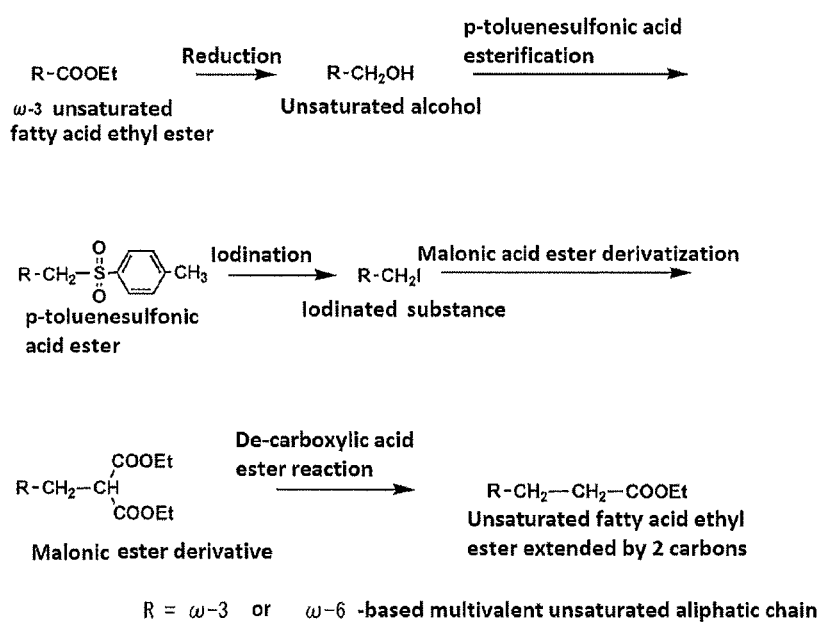

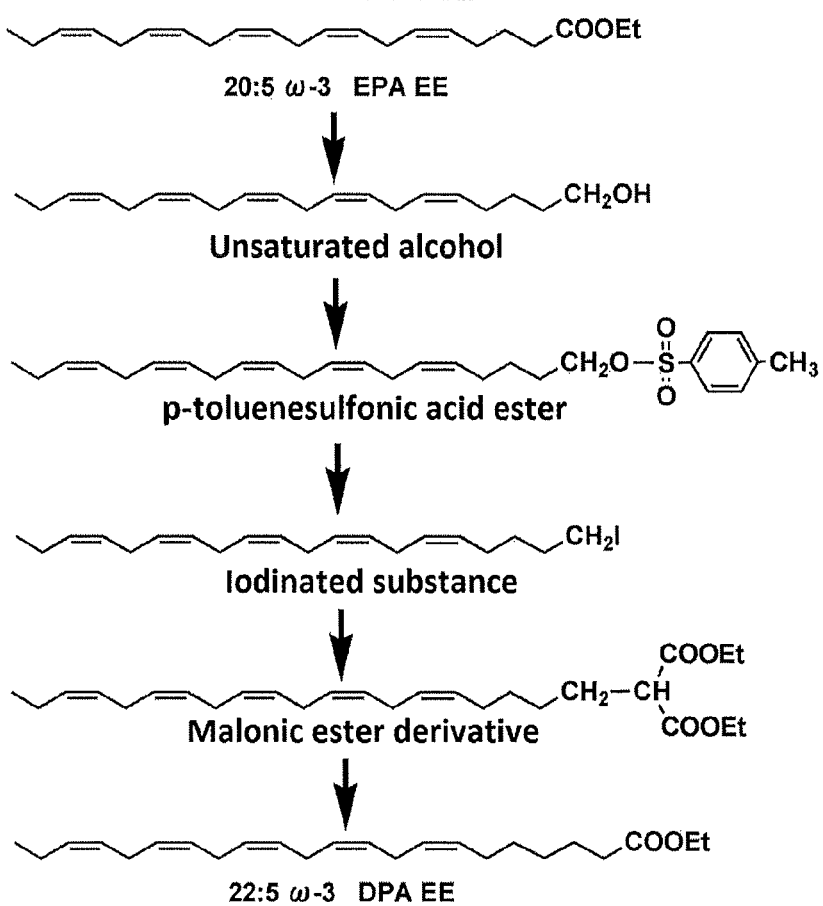

METHOD FOR CHEMICAL CONVERSION OF UNSATURATED FATTY ACID BY CARBON CHAIN EXTENSION REACTION

TECHNICAL FIELD

The present invention relates to a method of chemically converting an unsaturated fatty acid, especially a carbon chain extending reaction.

BACKGROUND ART

Docosapentaenoic acid is one of rare unsaturated fatty acids of C22: 5n-3 contained in fish oil in trace amounts. Since a highly pure docosapentaenoic acid cannot be obtained in large quantities, physiological, medical, and nutritional studies thereof have lagged behind (Non Patent Literature 1).

The following facts have been reported with respect to this point (Non Patent Literature 2).
(1) Docosapentaenoic acid is inversely converted into icosapentaenoic acid in many tissues.
(2) Docosapentaenoic acid is effective in maintaining and promoting health.
(3) Docosapentaenoic acid is metabolized in platelets to provide hydroxydocosapentaenoic acid.

The above facts suggest the possibility of docosapentaenoic acid being converted in vivo into resolvin D4, which activates the immune system to exhibit anti-inflammatory action.

Non Patent Literature 3 reports the following.
(4) Rabbit platelet agglutination inhibiting action of docosapentaenoic acid is more potent than icosapentaenoic acid or docosahexaenoic acid, and therefore a clot formation suppressing effect can be expected.
(5) Docosapentaenoic acid has endothelial cell migration capability that is 10-times greater than icosapentaenoic acid. This is an important effect in wound healing.

Non Patent Literature 4 reports the following.
(6) Docosapentaenoic acid has a more potent action of reducing fatty acid synthase and malate synthase activity than icosapentaenoic acid.
(7) Docosapentaenoic acid possibly regulates a phenomenon of sustained improvement in signaling between two nerve cells by costimulation and age-related spatial learning.

Non Patent Literature 5 reports the following.
(8) Docosapentaenoic acid has angiogenesis suppressing action.

As discussed above, docosapentaenoic acid would play an important role in fields of alternative medicines and health food in the future and see increased demand therewith. Thus, development of a highly efficient production method including the present invention is an urgent problem to be solved toward the future. In recent years, biofunction of multivalent unsaturated fatty acids, especially icosapentaenoic acid and docosapentaenoic acid derived from fish oil, has drawn attention. The demand thereof is about to increase even more, including highly pure icosapentaenoic acid as a medicament. The demand for multivalent unsaturated fatty acids as supplements, mainly docosapentaenoic acid, is also about to expand. Meanwhile, resources for multivalent unsaturated fatty acids are in a declining trend in a global scale, such that search for a method of preservation thereof is an important problem to be solved. While most multivalent unsaturated fatty acids are currently dependent on fishery resources including fish, research related to a method of production with algae or plant matters is actively pursed. For instance, Monsanto has established a method of producing stearidonic acid, which is a precursor to icosapentaenoic acid, with genetically modified soybeans, and the method is already approved by the FDA. Methods of using a reaction to chemically extend multivalent unsaturated fatty acids or a microbe produced desaturase have also been reported. However, it is generally difficult to simultaneously conduct a carbon chain extending reaction and desaturation on a large amount of multivalent unsaturated fatty acids, which is not at an implementable stage at a practical production level beyond the laboratory level. A chemical synthesis method of multivalent unsaturated fatty acids by a carbon chain extending reaction has been reported. For example in Non Patent Literature 6, one methylene proton in a p-toluenesulfonyl-methyl isocyanate molecule is pulled out with a base and the produced carbanion is reacted with saturated fatty acid methyl ester bromide to synthesize a new isocyanate having a carbon long chain, and a strong base such as sodium hydride is used to similarly replace the other proton of the methylene chain with an unsaturated chain. Lastly, lithium/ammonia/ethanol and methanol/hydrochloric acid are reacted to remove a toluene sulfonyl group and isonitrile group to synthesize a multivalent unsaturated fatty acid methyl ester. However, these methods are disadvantageous in that the total yield is low, and an expensive reagent or a reagent, which has a strong reactivity and is difficult to handle, must be used.

Meanwhile, Baba et al. have successfully synthesized tetracosahexaenoic acid with two more carbon atoms than docosahexaenoic acid ethyl ester through using docosahexaenoic acid ethyl ester as a starting material to produce alcohol by lithium aluminum hydride reduction and converting the alcohol to p-toluenesulfonic acid ester, and then converting the p-toluenesulfonic acid ester to iodide by a substitution reaction and, in the presence of a base, reacting diethylmalonate therewith to produce malonate ester, and subjecting the ester to alkaline hydrolysis, decarboxylation. (Non Patent Literature 7 and Non Patent Literature 8)

This reaction is also applied in a carbon chain extending reaction of linoleic acid or arachidonic acid. However, this method comprises many reaction steps and thus is not necessarily considered a practical method for large-scale production.

The method published by Ito et. al. in 2011 synthesizes tetracosahexaenoic acid with two more carbons in four steps from docosapentaenoic acid ethyl ester (Non Patent Literature 9). However, this method uses a reagent that is very unstable with respect to air called DIBAL-H and performs a reaction at a low temperature of −78° C. Thus, it is expected that scaling up the synthesis process would be difficult.

CITATION LIST

Non Patent Literature

[NPL 1] P. D. Nichols, J. Petrie, and S. Singh, Long-chain omega-3 oils—An update on sustainable sources. Nutrients, 2010, 2, 572-585.

[NPL 2] W. W. Christie, "Resolvins and protectins"— Chemistry and Biology, AOCS Lipid Library, Feb. 27, 2013.

[NPL 3] T. Kanayasu-Toyoda, I. Morita, and S. Murota, Docosapentaenoic acid (22:5, n-3), an elongation metabolite of eicosapentaenoic acid (20:5, n-3), is a potent stimulator of endothelial cell migration on pretreatment in vitro. Prostaglandins, Leucotrienes & EFA'S., 1996, 54, 319-325.

[NPL 4] G. Kaur, D. Cameron-Smith, M. Garg, A. J. Sinclair, Docosapentaenoic acid (22:5n-3): A review of its biological effects. Progress in Lipid Research, 2011, 50, 28-34.
[NPL 5] Tsuji, Morita (Tokyo Medical and Dental University) et. al., Japanese Journal of Circulation Research, 2002, 25, 5.
[NPL 6] D. W. Johnson, A synthesis of unsaturated very long chain fatty acids. Chem. Phys. Lipids, 1990, 56, 65-71.
[NPL 7] N. Baba, Md. K. Alam, Y. Mori, S. S. Haider, M. Tanaka, S. Nakajima and S. Shimizu, A first synthesis of a phosphatidylcholine bearing docosahexaenoic and tetracosahexaenoic acids. J. Chem. Soc. Perkin Trans. 1, 2001, 221-223.
[NPL 8] S. S. Haider, M. Tanaka, Md K. Alam, S. Nakajima, N. Baba, and S. Shimizu, Synthesis of phosphatidylcholine having a very long chain polyunsaturated fatty acid. Chem. Lett., 1998, 175-176.
[NPL 9] T. Itoh, A. Tomiyasu, and K. Yamamoto, Efficient synthesis of the very-long-chain n-3 fatty acids, tetracosahexaenoic acid (C24:6n-3) and tricosahexaenoic acid (C23:6n-3). Lipids, 2011, 46, 45-461.

SUMMARY OF INVENTION

Technical Problem

Methods of converting an unsaturated fatty acid into a different unsaturated fatty acid by chemically extending a carbon chain of the unsaturated fatty acid have been reported. One of such methods is a process of using a method of synthesizing malonic ester. The problem to be solved of the present invention is to shorten the reaction process of conventional methods to complete a carbon chain extending reaction in a shorter time.

Solution to Problem

The present invention improves conventional carbon chain extending reactions to shorten the overall reaction process. The inventors have completed the present invention by discovering that an unsaturated fatty acid ester extended by two carbons of interest can be obtained directly from an ester derivative (e.g., malonic ester derivative) of a long chain lipid (e.g., unsaturated fatty acid).

One aspect of the present invention provides a method of extending a carbon chain of an unsaturated fatty acid by two carbons by using a step of reacting a malonic ester derivative obtained from the unsaturated fatty acid and a lower fatty acid in the presence of an antioxidant.

One aspect of the present invention performs a carbon chain extending reaction on an unsaturated fatty acid by a method comprising: reducing and converting an unsaturated fatty acid ethyl ester into primary unsaturated alcohol; converting the alcohol to p-toluenesulfonic acid ester; converting the p-toluenesulfonic acid ester into an iodide; converting the iodide into malonic ester; and converting the malonic ester to an unsaturated fatty acid ester of interest with an extended carbon chain.

An unsaturated fatty acid or an ester thereof is synthesized into another unsaturated fatty acid with two more carbons according to the present invention. The method of the present invention was the first to be able to chemically synthesize a docosapentaenoic acid ethyl ester from an icosapentaenoic acid ethyl ester. The method of the present invention was able to obtain each of the following: icosatrienoic acid (C22: 2n-3)⇒icosatrienoic acid (C20: 2n-3) from α-linoleic acid; icosadienoic acid (C22: 2n-6) ⇒icosadienoic acid (C20: 2n-6) from linoleic acid; icosatetraenoic acid (C20: 4n-3) from stearidonic acid; docosatetraenoic acid (C22: 4n-6) from arachidonic acid; and tetracosahexaenoic acid (C24: 6n-3) from docosahexaenoic acid.

For example, the present invention also provides the following.
(Item 1)
A method of extending a carbon chain of an unsaturated fatty acid by two carbons, comprising reacting a malonic ester derivative obtained from the unsaturated fatty acid with a lower fatty acid in the presence of an antioxidant.
(Item 2)
The method of item 1, wherein the unsaturated fatty acid is an unsaturated fatty acid with 16-24 carbons.
(Item 3)
The method of item 1, wherein the unsaturated fatty acid is selected from the group selected from linoleic acid, linolenic acid, arachidonic acid, stearidonic acid, icosatetraenoic acid, icosapentaenoic acid, tetracosahexaenoic acid, and docosahexaenoic acid.
(Item 4)
The method of item 1, wherein the malonic ester derivative is a derivative selected from the group consisting of a diethyl malonate derivative, dimethyl malonate derivative, diisopropyl malonate derivative, and dibutyl malonate derivative.
(Item 5)
The method of item 1, wherein the lower fatty acid is a fatty acid with 1-7 carbons.
(Item 6)
The method of item 1, wherein the lower fatty acid is an acid selected from the group consisting of formic acid, propionic acid, acetic acid, butyric acid, isobutyric acid, valeric acid, pivalic acid, hydroangelic acid, and isovaleric acid.
(Item 7)
The method of item 1, wherein the antioxidant is butylhydroxytoluene.
(Item 8)
The method of item 1, which is carried out by heated reflux under a nitrogen atmosphere.

Advantageous Effects of Invention

According to the present invention, it is possible to synthesize a large quantity of a trace element, rare unsaturated fatty acid, contained in fish oil or the like to investigate unknown biofunction thereof. The present invention also has expectation for its potential as a method of synthesizing a useful unsaturated fatty acid from vegetable oil that is abundantly present in case of fish oil resource depletion in the future. The present invention was the first to be able to synthesize docosapentaenoic acid from icosapentaenoic acid.

BRIEF DESCRIPTION OF DRAWINGS

FIG. 1 shows a general diagram of a process of a carbon chain extending reaction.
FIG. 2 shows a representative carbon chain extending reaction process of the present invention.

DESCRIPTION OF EMBODIMENTS

The present invention is described hereinafter. Throughout the entire specification, a singular expression should be understood as encompassing the concept thereof in the plural form unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the terms commonly understood by those skilled in the art pertaining to the present invention. In case of a contradiction, the present specification (including the definitions) takes precedence. As used herein, "wt %" is interchangeably used with "percent concentration by mass"

Definition of Terms

The definitions of the terms especially used herein are listed hereinafter.

The term "unsaturated fatty acid" as used herein refers to fatty acid with one or more unsaturated carbon bonds. An unsaturated carbon bond refers to an unsaturated bond between carbons in a molecular chain of carbons, i.e., carbon double bond or triple bond. A naturally-occurring unsaturated fatty acid has one or more double bonds. Substitution thereof with a saturated fatty acid in a fatty acid imparts a change in the characteristic of fat such as melting point or fluidity.

In the present invention, an unsaturated fatty acid is preferably a multivalent unsaturated fatty acid. The number of carbons of the multivalent unsaturated fatty acid used in the present invention is not limited to, but is preferably 16-24, more preferably 17-23, and most preferably 18-22. The multivalent unsaturated fatty acid used in the present invention comprises preferably 1-7 and more preferably 2-6 double bonds. Examples of multivalent unsaturated fatty acids include, but are not limited to, linoleic acid, linolenic acid, arachidonic acid, stearidonic acid, icosatetraenoic acid, icosapentaenoic acid, docosahexaenoic acid and tetracosahexaenoic acid.

The term "antioxidant" used herein refers to a substance that attenuates or eliminates a harmful reaction involved with oxygen in the body, food, daily necessities, and industrial materials. A representative antioxidant includes, but is not limited to, butylhydroxytoluene.

The present invention provides a method of extending a carbon chain of an unsaturated fatty acid among malonic esters by two carbons by reacting a malonic ester with unsaturated aliphatic chain iodide in the presence of an antioxidant.

Besides butylhydroxytoluene, examples of antioxidants used in a method of extending a carbon chain of an unsaturated fatty acid by two carbons in the present invention include, but are not limited to, phenol derivatives such as butylhydroxyanisole, tocopherol, tocotrienol, polyphenols, flavonoids and derivatives thereof, ascorbic acid and sugar or lipid derivative thereof, tannins such as catechin, glutathione, melanoidin, caramel, uric acid, caramel, carotenoid, N-acetyl cysteine, lecithins, and glucose.

Examples of malonic esters available in the above-described method of extending a carbon chain of an unsaturated fatty acid by two carbons include, but are not limited to, diethyl malonate, dimethyl malonate, diisopropyl malonate, dibutyl malonate and the like.

The number of carbons of a lower fatty acid used in the carbon chain extending reaction of the present invention is not limited to, but is preferably 1-7, more preferably 2-6, and most preferably 2-5. Examples of the lower fatty acid used in the present invention include, but are not limited to, formic acid, propionic acid, acetic acid, butyric acid, isobutyric acid, valeric acid, pivalic acid, hydroangelic acid, and, isovaleric acid. The amount of lower fatty acid added (added mass) is not particularly limited, but is typically twice or more of the mass of reaction mixture other than the lower fatty acid. Preferably, mass of reaction mixture other than lower fatty acid: mass of added lower fatty acid=1:2-1:20.

Malonic esters used in the method of extending a carbon chain of an unsaturated fatty acid by two carbons in a malonic ester derivative of unsaturated fatty acid of the present invention can be manufactured by any well-known method.

For example, the present invention can produce a malonic ester derivative obtained from an unsaturated fatty acid by a method comprising:

(a) reducing an unsaturated fatty acid or an ester thereof to produce unsaturated alcohol;
(b) converting the unsaturated alcohol to a p-toluenesulfonic acid ester;
(c) using the p-toluenesulfonic acid ester to produce an iodide or bromide of the unsaturated fatty acid; and
(d) converting the iodide into a malonic ester derivative.

For example, the invention of the present application provides a method of extending a carbon chain of an unsaturated fatty acid by two carbons by further performing (e) reacting the malonic ester derivative with a lower fatty acid in the presence of an antioxidant, following the above-described steps.

The above-described (a) is performed, for example, by reducing a multivalent unsaturated fatty acid or an ester thereof with lithium aluminum hydride in a dried tetrahydrofuran solvent to produce unsaturated alcohol. In addition to tetrahydrofuran, dimethyl ether, diethyl ether, dipropyl ether, or diisopropyl ether may be used as the solvent used in this reaction. Instead of lithium aluminum hydride used in this reaction, the following compound can be used: sodium bis(2-methoxyethoxy)aluminum hydride, lithium borohydride, diisobutylaluminum hydride [DIBAL], aluminum hydride, sodium borohydride+aluminum chloride, lithium triethylborohydride, Grignard reagents, borane, lithium hydrotriethylborate, triacetoxyborohydride [sodium triacetoxyborohydride], sodium borohydride+ethanedithiol, sodium trimethoxyborohydride, and lithium amidotrihydroborate. However, the compounds are not limited thereto. Any solvent can be used as long as a reduction reaction from an ester to alcohol is possible.

In the above-described step (b), unsaturated alcohol is converted into p-toluenesulfonic acid ester or benzenesulfonic acid ester. Alternatively, the above-described (b) converts unsaturated alcohol into a compound with a structural feature of an ester of an acid in which a sulfonic acid group is bound to an aromatic ring such as benzene or toluene.

When an iodide is produced in the above-described (c), for example, lithium iodide, sodium iodide, potassium iodide or a mixture thereof can be used. When a bromide is generated in the above-described (c), for example, lithium bromide, sodium bromide, potassium bromide or a mixture thereof can be used.

The above-described step (d) is performed, for example, by reacting a base with diethyl malonate to produce carbanion, which is reacted with the iodide for conversion into malonate diester bound to an unsaturated fatty chain. It is possible to use dimethyl malonate, diisopropyl malonate, dibutyl malonate, diisobutyl malonate, di-sec-butyl malonate or the like instead of diethyl malonate. Further, examples of the base include sodium hydride, lithium hydride, potassium hydride, lithium hydroxide, sodium hydroxide, potassium hydroxide, sodium amide, lithium amide, potassium amide and the like.

In the above-described (e), for example, a malonic ester derivative can be used as a solution of lower fatty acid such as propionic acid for 1-50 hours of heated reflux after adding an antioxidant under a nitrogen atmosphere to obtain a fatty acid ester extended by 2 carbons of interest. In addition, it is possible to use formic acid, acetic acid, butyric acid, isobutyric acid, valeric acid, pivalic acid, hydroangelic acid, or isovaleric acid instead of propionic acid.

The present invention performs a carbon chain extending reaction based on malonic ester synthesis while replacing each reaction in the synthesis pathway with a more efficient reaction and further incorporating a new reaction to omit conventional reactions, construct a novel carbon chain extending reaction pathway, and efficiently synthesize rare lipids including docosapentaenoic acid or ethyl ester thereof. For instance, this is a method of manufacturing rare lipids including docosapentaenoic acid of interest or an ester thereof by reducing a multivalent unsaturated fatty acid ethyl ester including icosapentaenoic acid or an ester thereof with lithium aluminum hydride to produce multivalent unsaturated alcohol, which is converted into p-toluenesulfonic acid ester (or ester of an acid in which a sulfonic acid group is bound to an aromatic ring such as benzene or toluene) with a method that does not use pyridine that is malodorous and difficult to handle and then reacted with lithium iodide to derive a multivalent unsaturated fat iodide, and in the presence of alkali, reacting diethyl malonate with the iodide to synthesize a malonic acid derivative and heating the propionic acid solution of the derivative (see the Mentioned Reference: R. T. Brown and M. F. Jones, Dealkoxycarbonylation of representative β-keto-esters and β-diesters in alkanoic acids. J. Chem. Res. (S). 1984, 332-333, FIG. 1).

This last step would include three steps in conventional methods, i.e., synthesis of dicarboxylic acid by hydrolysis of a malonic acid derivative, synthesis of monocarboxylic acid by decarboxylation under acidic condition, and ethyl esterification of the carboxylic acid. These steps are complex while having low overall yield.

The present invention is explained in detail hereinafter for exemplification. The technical scope of the present invention is set forth by the Claims and is not limited by the following description.

Synthesis of a malonic ester, which is the main reaction in the synthesis process in the present invention, is a reaction that is extensively used in conversion of an organic compound into carboxylic acid with two additional carbon atoms or, for aliphatic chains, synthesis of carboxylic acid extended by 2 carbon atoms or an ester thereof. The present invention materializes a series of chemical reactions including this reaction with improvement.

A synthesis reaction scheme 1 of the present invention is shown (FIG. 1). (1) A multivalent unsaturated fatty acid or an ester thereof is reduced with lithium aluminum hydride in a dried tetrahydrofuran solvent to produce unsaturated alcohol. (2) For conversion into a malonic ester derivative, this alcohol is converted into a p-toluenesulfonic acid ester and reacted with lithium iodide to produce an iodide. (3) A base is reacted with diethyl malonate to produce carbanion, which is reacted with the iodide in (2) and converted into malonic acid diester which binds to an unsaturated aliphatic chain. (4) As the final step, the diester is used as a solution of lower fatty acid such as propionic acid for 1-50 hours of heated reflux after adding an antioxidant under a nitrogen atmosphere to obtain an unsaturated fatty acid ester extended by 2 carbons of interest.

Synthesis of a malonic ester, which is the main reaction in the synthesis process in the present invention, is a reaction that is extensively used in conversion of an organic compound into carboxylic acid with two additional carbon atoms or, for aliphatic chains, synthesis of carboxylic acid extended by 2 carbon atoms or an ester thereof. The present invention materializes a series of chemical reactions including this reaction with improvement.

The raw materials in the present invention are obtained by urea treatment, silver nitrate treatment, vacuum distillation, column chromatography including SMB, or a combination thereof from multivalent unsaturated fatty acids or alcohol esters thereof obtained from fish, seaweed, microorganisms, plant or chemical synthesis. Multivalent unsaturated fatty acids or alcohol esters thereof used as the starting material of synthesis are preferably highly pure, but starting materials with low purity can be used without any issues as purification is performed in each stage of synthesis.

The first step is a conversion reaction from an ester to primary alcohol with a reducing reagent, lithium aluminum hydride. Among various reducing reagents, lithium aluminum hydride is used at overwhelmingly high frequency as a reagent for converting esters to alcohol. This is due to such a reagent being highly reactive while hardly affecting carbon-carbon unsaturated bonds. In view of such properties, the reagent can be used without any issues in chemical conversion of icosapentaenoic acid, docosapentaenoic acid, and esters thereof to primary alcohol. Further, any ether without a leaving group such as diethyl ether and tetrahydrofuran can be used as a reaction solvent. After completion of a reaction, primary alcohol of interest can be readily obtained only by adding an excessive amount of ethyl acetate and completely using up unreacted residual lithium aluminum hydride, dissolving alkoxide generated as a byproduct by adding an aqueous caustic soda solution, filtering the separated hydroxide, and concentrating the filtrate. Further, a substance of interest with high purity can be readily obtained by purification with column chromatography as needed, which can be used directly in the next reaction.

The objective of the present invention can be achieved theoretically by replacing a hydroxyl group of unsaturated alcohol with an ethoxycarbonylmethyl group $CH_2COOEt$, but in practice, the step discussed below is required. A hydroxyl group must be detached in order to have another carbon bind to a carbon atom to which the hydroxyl group is bound. To facilitate a hydroxyl group in leaving, a hydroxyl group is generally converted to a p-toluenesulfonic acid ester and then the p-toluenesulfonic acid ester moiety is replaced with iodine. Such a p-toluenesulfonic acid ester generally exhibits instability with respect to heat or the like and is thus unsuitable for introduction of a malonyl group which requires heating for an extended period of time. Other than iodine, bromine or chlorine may be used. However, softer iodine is optimal for introduction of a malonyl group. Although a method of directly replacing a hydroxyl group with iodine is available, this reaction condition would significantly break down double bonds. Thus, there is a risk of the reaction conditions for replacing a hydroxyl group with a halogen atom inducing break down of all cis form non-conjugated double bonds of EPA or DHA.

A long chain unsaturated lipid iodide is synthesized by reacting lithium iodide with primary alcohol obtained from an unsaturated fatty acid ester while considering the above conditions. While sodium iodide or potassium iodide may be used instead of lithium iodide used in this reaction, lithium iodide is preferable in view of issues of solubility into an organic solvent. Such an iodination reaction is performed in dried acetone. After completing the reaction, a substance of interest is obtained if precipitation of sodium iodide is filtered and filtrate is concentrated and then the residue is purified by silica gel column, so that the substance of interest can be converted into the next malonic ester derivative.

When a base, i.e., sodium hydride, is reacted with diethyl malonate, a carbon anion of diethyl malonate is produced. This ion attacks carbon bound to p-toluenesulfonic acid to produce a carbon-carbon bond. Extension by two carbon atoms is first materialized with this reaction. However, since a product with an extended carbon chain produced as a result of this reaction has a COOEt group derived from malonic acid, this must be removed.

A general removal method thereof first reacts alkali with a malonic diester derivative for hydrolysis, and heats the produced dicarboxylic acid in acetic acid for decarboxylation. The resulting monocarboxylic acid undergoes the process of being converted to an ethyl ester to obtain the final product of interest. However, in order to avoid such complexity, the present invention has found that an unsaturated fatty acid ester extended by 2 carbons of interest can be obtained directly from a malonic ester derivative of a long chain lipid by application of the method published by Brown and Jones in 1984. With this method, the substance of interest is obtained only from heated reflux of a propionic acid solution of malonic ester derivative of a long chain lipid, removal of the solvent, and column purificationd.

While the present invention is explained in detail with the following Examples and the like, the present invention is not limited thereto.

EXAMPLE

Example 1

100 ml of dried tetrahydrofuran was placed in a 2-liter reaction flask, and 7.34 g of lithium aluminum hydride was carefully added thereto. After stirring for 5 minutes with a magnetic stirrer, dried tetrahydrofuran solution (210 ml) of 44.6 g (0.135 mol) of icosapentaenoic acid ethyl ester was slowly dripped into the suspension while stirring, such that the reaction would not be too intense. The solution was cooled with ice water as needed. After 5 hours of reaction at room temperature, the reaction flask was cooled to 0-5° C. from the outside with ice water, and ethyl acetate (about 100 ml) was slowly dripped in to consume the residual unreacted lithium aluminum hydride. Subsequently, an aqueous 2N sodium hydroxide solution (about 60 ml) was dripped in while stirring in order to break down a reaction complex. Dripping was discontinued when a grey insoluble matter began to separate from the reaction solution. The solution was filtered with filter paper to remove insoluble matters. The filtrate was washed twice (70 ml×2) with an aqueous 2N hydrochloric acid solution. Subsequently, the filtrate was washed twice with saturated aqueous sodium bicarbonate and twice with saturated saline, and dried with anhydrous magnesium sulfate. Magnesium sulfate was separated by filtration, and the filtrate was concentrated under reduced pressure. Column (diameter 4.5 cm) purification was then performed by using about 70 ml of silica gel (C-60 Nacalai Tesque) with hexane/ethyl acetate (9:1) solvent mixture as an eluate. The yield was 30.4 g (yield 78.1%).

A dried pyridine (about 70 ml) solution of the above-described alcohol (30.4 g, 0.105 mol) was placed in a 1-liter reaction flask equipped with a temperature gauge and a nitrogen gas feeding tube as shown in FIG. 1. p-Toluenesulfonic acid chloride was gradually added while stirring with a magnetic stirrer at 1-5° C. under a nitrogen atmosphere. After completing the addition, the solution was stirred for 5 hours at around 1° C. After completion of the reaction, the reaction solution was diluted with about 100 ml of methylene chloride, washed four times with an aqueous 2N hydrochloric acid solution, and then dried with anhydrous magnesium sulfate. Since a p-toluenesulfonic acid ester is generally unstable, the residual from removing the solvent under reduced pressure was directly used in the next reaction.

An acetone solution (188 ml) dried with a 4A molecular sieve of 12.4 g (0.093 mol) of lithium iodide and 41.0 g (0.093 mol) of the above-described p-toluenesulfonic acid ester was placed in a 500 ml reaction flask to which a cooling tube and a nitrogen balloon were attached, heated, and refluxed for 4 hours while stirring with a magnetic stirrer under a nitrogen atmosphere. It is necessary to be careful at this time for fierce bumping. After cooling, produced lithium p-toluenesulfonate crystals were filtrated out to extract the substance of interest from the filtrate 4 times with hexane. The hexane solution, after washing with saturated saline, was dried with anhydrous magnesium sulfate, and the residual obtained from removing the solvent under reduced pressure was purified with silica gel column. Hexane/ethyl acetate (9:1) mixed solvent was used as an eluate. The yield was 28.0 g (yield 76%).

Sixty % pure sodium hydride (3.58 g) was measured out into a 1-liter reaction flask, and the oil covering the surface for protection from moisture was removed by washing three times with hexane. Specifically, after adding about 20 ml of hexane and gently stirring and leaving the mixture standing, the supernatant was removed with a pipette. This operation was repeated three times. A solvent mixture of dried dimethylformamide (200 ml) and dried tetrahydrofuran (200 ml) was added to the sodium hydride. To this solution, a solution comprising diethylmalonate (14.3 g, 0.084 mol) dissolved into the above-described solvent mixture (60 ml) was added, and stirred for 20 minutes at room temperature under a nitrogen atmosphere. After dripping in, to this solution, a solution comprising iodide (28 g), which was synthesized as described above, dissolved into a solvent mixture of dried dimethylformamide (30 ml) and dried tetrahydrofuran (30 ml), the solution was heated for 6 hours at 70-80° C. After cooling, a substance of interest was extracted from the reaction solution by two hexane extraction (200 ml×2), and the solution was washed three times with water. After drying with anhydrous sodium sulfate, the solution was purified with silica gel column (silica gel 200 ml, column (diameter 4 cm), hexane/ethyl acetate (98:2)) to obtain 15.7 g of malonic acid derivative. The yield was 15.7 g (yield 51.6%).

A small amount of antioxidant BHT was added to a propionic acid (20 ml) solution of the malonic acid ester derivative (0.92 g) described above under a nitrogen atmosphere and the solution refluxed for 38 hours. The same reaction can be performed with a minimum amount of 2 ml of propionic acid, but 20 ml is desirable. The solution was also washed with diethyl ether (20 ml) and the reaction solution was transferred to a separating funnel, and hexane (80 ml) was added and washed with water (20 ml×3) to remove the residual propionic acid. Subsequently, the solution was washed twice with saturated aqueous sodium bicarbonate and twice with saturated saline, and then dried with anhydrous sodium sulfate. The solvent was removed under reduced pressure and the residual was purified with silica gel column to obtain 0.6 g of final substance of interest, docosapentaenoic acid ethyl ester. The yield was 9.7 g (yield 73.9%).

Example 2

It was possible to synthesize icosadienoic acid (C20: 2n-6) from linoleic acid (C18: 2n-6) by the same method.

Example 3

It was possible to synthesize icosatetraenoic acid (C20: 4n-3) from stearidonic acid (C18: 4n-3) by the same method.

Example 4

It was possible to synthesize docosatetraenoic acid (C22: 4n-6) from arachidonic acid (C20: 4n-6) by the same method.

Example 5

It was possible to synthesize tetracosahexaenoic acid (C24: 6n-3) from docosahexaenoic acid by the same method.

INDUSTRIAL APPLICABILITY

The present invention can chemically synthesize rare multivalent unsaturated fatty acids which are contained in fish oil or the like at very small amounts by a carbon chain extending reaction without depending on organisms or enzymes. The ability to obtain sufficient amount of rare multivalent unsaturated fatty acid in this manner would not only be a valuable material for studying the physicochemical property, biochemical property, or biofunction thereof, but is also expected to lead to successful development of a medicament.

The invention claimed is:

1. A method of extending a carbon chain of an unsaturated fatty acid by two carbons, comprising reacting a malonic ester derivative obtained from the unsaturated fatty acid with a lower fatty acid in the presence of an antioxidant.

2. A method of extending a carbon chain of an unsaturated fatty acid by two carbons, comprising reacting a malonic ester derivative obtained from the unsaturated fatty acid with a lower fatty acid, wherein the unsaturated fatty acid is an unsaturated fatty acid with 16-24 carbons and comprises 2-6 double bonds, and the lower fatty acid is a fatty acid with 2-7 carbons.

3. The method of claim 1 or 2, wherein the unsaturated fatty acid is selected from the group selected from linoleic acid, linolenic acid, arachidonic acid, stearidonic acid, icosatetraenoic acid, icosapentaenoic acid, tetracosahexaenoic acid, and docosahexaenoic acid.

4. The method of claim 1 or 2, wherein the malonic ester derivative is a derivative selected from the group consisting of a diethyl malonate derivative, dimethyl malonate derivative, diisopropyl malonate derivative, and dibutyl malonate derivative.

5. The method of claim 1 or 2, wherein the lower fatty acid is an acid selected from the group consisting of formic acid, propionic acid, acetic acid, butyric acid, isobutyric acid, valeric acid, pivalic acid, hydroangelic acid, and isovaleric acid.

6. The method of claim 1, wherein the antioxidant is butylhydroxytytoluene.

7. The method of claim 1 or 2, which is carried out by heated reflux under a nitrogen atmosphere.

* * * * *